US012655378B2

(12) United States Patent
Hagiwara

(10) Patent No.: US 12,655,378 B2
(45) Date of Patent: Jun. 16, 2026

(54) CELL CULTURE CONTAINER, FIXING TOOL, OBSERVATION DEVICE, MICROSCOPE AND OBSERVATION METHOD

(71) Applicant: RIKEN, Saitama (JP)

(72) Inventor: Masaya Hagiwara, Saitama (JP)

(73) Assignee: RIKEN, Saitama (JP)

( * ) Notice: Subject to any disclaimer, the term of this patent is extended or adjusted under 35 U.S.C. 154(b) by 884 days.

(21) Appl. No.: 17/924,159

(22) PCT Filed: May 11, 2021

(86) PCT No.: PCT/JP2021/017794
§ 371 (c)(1),
(2) Date: Nov. 9, 2022

(87) PCT Pub. No.: WO2021/230220
PCT Pub. Date: Nov. 18, 2021

(65) Prior Publication Data
US 2023/0174911 A1     Jun. 8, 2023

(30) Foreign Application Priority Data

May 11, 2020    (JP) ................................. 2020-083426

(51) Int. Cl.
| *C12M 1/00* | (2006.01) |
| *C12M 1/34* | (2006.01) |
| *G02B 21/26* | (2006.01) |

(52) U.S. Cl.
CPC ............ *C12M 23/22* (2013.01); *C12M 41/12* (2013.01); *C12M 41/34* (2013.01); *G02B 21/26* (2013.01)

(58) Field of Classification Search
CPC ...... C12M 23/22; C12M 41/12; C12M 41/34; C12M 23/02; C12M 25/14; C12M 41/36; G02B 21/26; G02B 21/34
See application file for complete search history.

(56) References Cited

U.S. PATENT DOCUMENTS 10,793,816 B2 * 10/2020 Weinberger ............ C12M 25/14
2019/0002812 A1     1/2019 Hagiwara et al.
(Continued)

FOREIGN PATENT DOCUMENTS

| EP | 3 584 307 A1 | 12/2019 |
| EP | 4 230 719 A1 | 8/2023 |
(Continued)

OTHER PUBLICATIONS

Written Opinion for PCT/JP2021/017794 and its English Translation, dated Aug. 3, 2021, 8 pages.
(Continued)

*Primary Examiner* — Jennifer Wecker
*Assistant Examiner* — Britney N. Washington
(74) *Attorney, Agent, or Firm* — Casimir Jones, S.C.; Robert A. Goetz

(57) ABSTRACT

Provided is a cell culture vessel which allows resolution to be high in a Z-axis direction. A cell culture vessel (1) for accommodating a cell or cell tissue therein includes: a frame part (11) which is provided so as to be located at positions that correspond to respective sides of a polyhedral shape; a window part (12) which is light-transmissive and which is provided so as to be located at positions that correspond to a respective plurality of faces out of faces of the polyhedral shape; and a shaft part (17) which extends, from any of vertices of the polyhedral shape, outward in a direction that is not parallel to any of lines normal to the faces of the polyhedral shape.

16 Claims, 12 Drawing Sheets

(56) References Cited

U.S. PATENT DOCUMENTS

| | | | | |
|---|---|---|---|---|
| 2020/0017814 A1* | 1/2020 | Hagiwara | .............. | C12M 25/14 |
| 2020/0032186 A1* | 1/2020 | Hagiwara | .............. | C12M 25/16 |
| 2020/0264204 A1* | 8/2020 | Negatu | ................. | G02B 21/26 |
| 2022/0325240 A1* | 10/2022 | McFarland | ............ | A61K 40/24 |

FOREIGN PATENT DOCUMENTS

| | | |
|---|---|---|
| JP | 2016-124057 | 7/2016 |
| WO | 2018/147032 | 8/2018 |
| WO | 2018/150689 | 8/2018 |

OTHER PUBLICATIONS

International Search Report for PCT/JP2021/017794 and its English Translation, dated Aug. 3, 2021, 4 pages.

Masaya Hagiwara et al.: "Tissue in Cube:In Vitro 3D Culturing Platform with Hybrid Gel Cubes for Multidirectional Observations", Advanced Healthcare Materials, vol. 5, No. 13, Jul. 1, 2016 (Jul. 1, 2016), pp. 1566-1571, XP055620295, DE ISSN: 2192-2640, DOI:10.1002/adhm.201600167.

Extended European search report for EP Patent Application No. 21803722.4, dated Jun. 6, 2025, 8 pages.

* cited by examiner

CELL CULTURE CONTAINER, FIXING TOOL, OBSERVATION DEVICE, MICROSCOPE AND OBSERVATION METHOD

TECHNICAL FIELD

The present invention relates to a cell culture vessel, a fixing tool, an observation apparatus, a microscope, and an observation method.

BACKGROUND ART

As a method of observing a three-dimensional structure of a cell or cell tissue, a method has been suggested which involves (i) accommodating a cell or cell tissue, which is a target of an observation, in a cell culture vessel that has a cubic shape and that includes light-transmissive window parts provided at positions corresponding to respective faces of the cubic shape and (ii) observing the target from each of the window parts. In this observation method, images each of which shows the target that is sliced in a horizontal direction (hereinafter also referred to as "X-Y direction") of the cell culture vessel having a cubic shape are scanned in a vertical direction (hereinafter also referred to as "Z direction") to obtain a three-dimensional image of the target (see Patent Literature 1).

In the above observation method, in a case where relatively large cell tissue such as an organoid is targeted, only a low-magnification objective lens can be used. Therefore, the depth of focus is deep, and accordingly only images that have low resolution in a Z-axis direction and that are therefore unclear can be obtained. In order to solve this problem, while the cell culture vessel having a cubic shape is being held with use of tweezers or the like and is being manually rotated, the target is observed from a plurality of faces which constitute the cubic shape. As a result, by interpolation between pieces of image data which are obtained by observing the target from the plurality of faces, it is possible to improve the resolution of images in the Z-axis direction.

However, in the above-described observation method, it is necessary to hold the cell culture vessel with use of tweezers or the like and rotate the cell culture vessel. This imposes a large burden on an observer.

CITATION LIST

Patent Literature

[Patent Literature 1]
International Application Publication No. 2017-094451 (published on Jun. 8, 2017)

SUMMARY OF INVENTION

Technical Problem

Under the circumstances, the object of the present invention is to provide a cell culture vessel, a fixing tool for fixing a cell culture vessel, an observation apparatus including a cell culture vessel, a microscope including an observation apparatus, and a method of observing a cell or cell tissue accommodated in a cell culture vessel, each of which is capable of reducing a burden on an observer.

Solution to Problem

In order to attain the above object, a cell culture vessel in accordance with an aspect of the present invention is a cell culture vessel for accommodating a cell or cell tissue therein, including: a frame part which is provided so as to be located at positions that correspond to respective sides of a polyhedral shape; a window part which is light-transmissive and which is provided so as to be located at positions that correspond to a respective plurality of faces out of faces of the polyhedral shape; and a shaft part which extends, from any of vertices of the polyhedral shape, outward in a direction that is not parallel to any of lines normal to the faces of the polyhedral shape.

In order to attain the above object, an observation apparatus in accordance with an aspect of the present invention is an observation apparatus including a rotating mechanism which holds a shaft part of a cell culture vessel and which rotates the cell culture vessel on the shaft part, the cell culture vessel being for accommodating a cell or cell tissue therein, the cell culture vessel including: a frame part which is provided so as to be located at positions that correspond to respective sides of a polyhedral shape; a window part which is light-transmissive and which is provided so as to be located at positions that correspond to a respective plurality of faces out of faces of the polyhedral shape; and the shaft part which extends, from any of vertices of the polyhedral shape, outward in a direction that is not parallel to any of lines normal to the faces of the polyhedral shape.

In order to attain the above object, a fixing tool in accordance with an aspect of the present invention is a fixing tool for fixing a cell culture vessel for accommodating a cell or cell tissue therein, the cell culture vessel including: a frame part which is provided so as to be located at positions that correspond to respective sides of a polyhedral shape; and a window part which is light-transmissive and which is provided so as to be located at positions that correspond to a respective plurality of faces out of faces of the polyhedral shape, the fixing tool including: a holding part which holds the cell culture vessel; and a shaft part which is connected to the holding part and which extends, from any of vertices of the polyhedral shape, outward in a direction that is not parallel to any of lines normal to the faces of the polyhedral shape.

In order to attain the above object, an observation apparatus in accordance with an aspect of the present invention is an observation apparatus including: a fixing tool for fixing a cell culture vessel for accommodating a cell or cell tissue therein; and a rotating mechanism which rotates the cell culture vessel, the cell culture vessel including: a frame part which is provided so as to be located at positions that correspond to respective sides of a polyhedral shape; and a window part which is light-transmissive and which is provided so as to be located at positions that correspond to a respective plurality of faces out of faces of the polyhedral shape, the fixing tool including: a holding part which holds the cell culture vessel; and a shaft part which is connected to the holding part and which extends, from any of vertices of the polyhedral shape, outward in a direction that is not parallel to any of lines normal to the faces of the polyhedral shape, the rotating mechanism holding the shaft part and rotating, on the shaft part, the cell culture vessel held by the fixing tool.

In order to attain the above object, an observation method in accordance with an aspect of the present invention is a method of observing a cell culture vessel for accommodating a cell or cell tissue therein, the cell culture vessel including: a frame part which is provided so as to be located at positions that correspond to respective sides of a polyhedral shape; a window part which is light-transmissive and which is provided so as to be located at positions that correspond to a respective plurality of faces out of faces of the polyhedral shape; and a shaft part which extends, from any of vertices of the polyhedral shape, outward in a direction that is not parallel to any of lines normal to the faces of the polyhedral shape, the method including: holding the shaft part of the cell culture vessel and rotating the cell culture vessel on the shaft which is not parallel to any of the lines normal to the faces of the polyhedral shape of the cell culture vessel; and observing the cell or the cell tissue from the plurality of faces out of the faces of the polyhedral shape while rotating the cell culture vessel.

In order to attain the above object, an observation method in accordance with an aspect of the present invention is a method of observing a cell or cell tissue accommodated in a cell culture vessel, the cell culture vessel including: a frame part which is provided so as to be located at positions that correspond to respective sides of a polyhedral shape; and a window part which is light-transmissive and which is provided so as to be located at positions that correspond to a respective plurality of faces out of faces of the polyhedral shape, a fixing tool for fixing the cell culture vessel including: a holding part which holds the cell culture vessel; and a shaft part which is connected to the holding part and which extends, from any of vertices of the polyhedral shape, outward in a direction that is not parallel to any of lines normal to the faces of the polyhedral shape, the method including holding the cell culture vessel with use of the fixing tool and rotating the cell culture vessel on the shaft part.

Advantageous Effects of Invention

According to aspects of the present invention, it is possible to realize a cell culture vessel, a fixing tool for fixing a cell culture vessel, an observation apparatus, a microscope, and an observation method, each of which is capable of reducing a burden on an observer.

BRIEF DESCRIPTION OF DRAWINGS

FIG. 3 is a drawing illustrating a state in which the fixing tool illustrated in FIG. 2 is fitted on the cell culture vessel.

FIG. 4 is a perspective view illustrating a state in which an observation apparatus in accordance with Embodiment 1 of the present invention is mounted on a microscope.

DESCRIPTION OF EMBODIMENTS

Embodiment 1

The following description will discuss an embodiment of the present invention in detail.

<Cell Culture Vessel>

Figure 1:
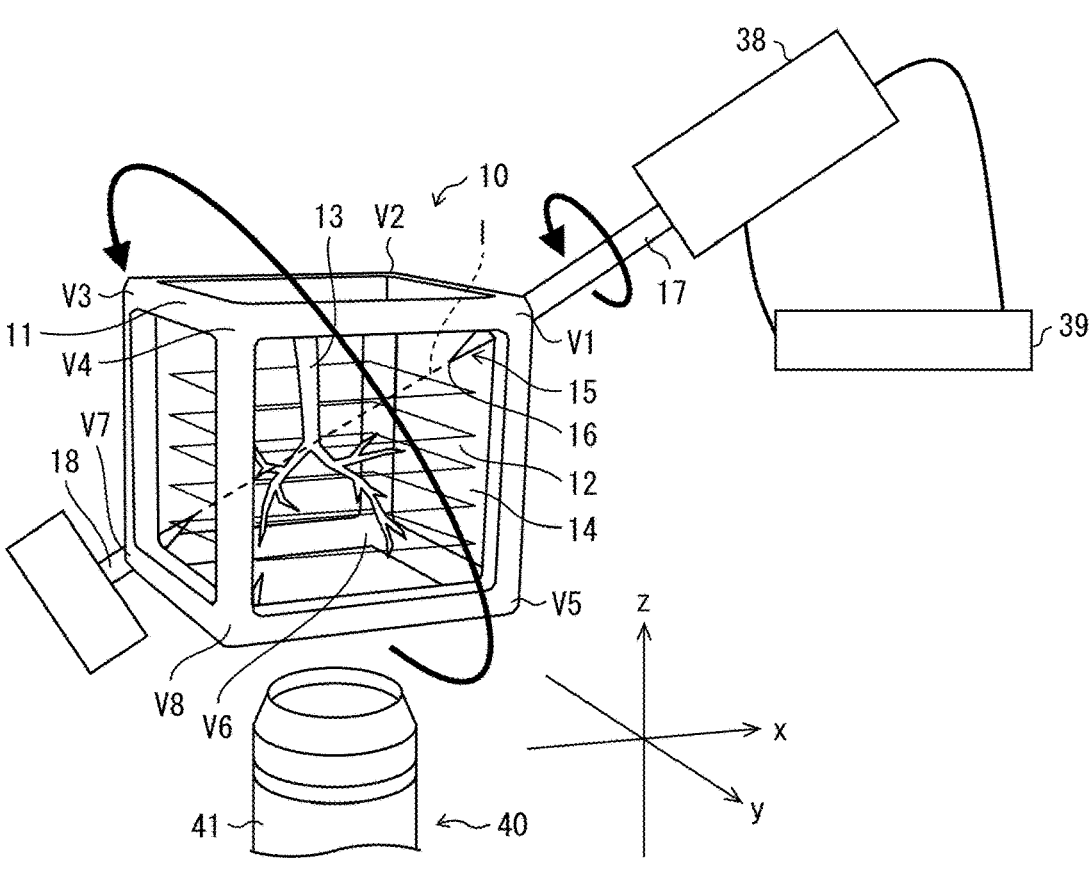
FIG. 1 is a perspective view illustrating examples of a cell culture vessel and a fixing tool in accordance with Embodiment 1 of the present invention.

FIG. 1 is a perspective view illustrating examples of a cell culture vessel 10 and a fixing tool 20 in accordance with Embodiment 1 of the present invention. First, the cell culture vessel 10 in accordance with Embodiment 1 will be described with reference to FIG. 1.

The cell culture vessel 10 is a vessel for accommodating and culturing a cell or cell tissue therein. The cell culture vessel 10 in accordance with Embodiment 1 of the present invention is configured to have, for example, a substantially cubic shape, as illustrated in FIG. 1. More specifically, as illustrated in FIG. 1, the cell culture vessel 10 has a substantially cubic shape having eight vertices, i.e., vertices V1, V2, V3, V4, V5, V6, V7, and V8. Note, however, that the shape of the cell culture vessel 10 is not limited to a cubic shape, and may have another polyhedral shape, such as a rectangular parallelepiped shape, or a spherical shape. Note that the cell culture vessel 10 preferably has a hexahedral shape, and more preferably has a cubic shape, from the viewpoint of ease of handling of the cell culture vessel 10 and appropriate obtainment of image information in a z-axis direction. The size of the cell culture vessel 10 can be, for example, such that each side of a cube has an outer dimension of approximately 4 mm and an inner dimension of approximately 3 mm. Note, however, that the specific size of the cell culture vessel 10 does not limit Embodiment 1.

As illustrated in FIG. 1, the cell culture vessel 10 includes: a frame part 11 which is provided so as to be located at positions that correspond to respective sides of a polyhedral shape (cubic shape); and a window part 12 which is light-transmissive and which is provided so as to be located at positions that correspond to a respective plurality of faces out of faces of the polyhedral shape. That is, the frame part 11 of the cell culture vessel 10 is constituted by portions which correspond a total of 12 sides (sides defined by (i) the vertices V1 and V2, (ii) the vertices V2 and V3, (iii) the vertices V3 and V4, (iv) the vertices V4 and V1, (v) the vertices V5 and V6, (vi) the vertices V6 and V7, (vii) the vertices V7 and V8, (viii) the vertices V8 and V5, (ix) the vertices V1 and V5, (x) the vertices V2 and V6, (xi) the vertices V3 and V7, and (xii) the vertices V4 and V8) constituting the cubic shape illustrated in FIG. 1. A material of the frame part 11 may be, for example, a biocompatible resin such as polycarbonate.

The window part 12 is surrounded by the 12 sides constituting the frame part 11. That is, the window part 12 is constituted by six faces (i.e., a face constituted by V1, V2, V3, and V4, a face constituted by V1, V2, V6, and V5, a face constituted by V2, V3, V7, and V6, a face constituted by V3, V4, V8, and V7, a face constituted by V1, V4, V8, and V5, and a face constituted by V5, V6, V7, and V8) constituting the cubic shape illustrated in FIG. 1. A material of the window part 12 is preferably a material which is light-transmissive and which is permeable to a nutrient, a stimulating factor, and/or the like necessary to culture the cell or cell tissue (hereinafter also referred to as "sample") accommodated in the cell culture vessel 10. Specifically, the material of the window part 12 preferably contains agarose gel, polyacrylamide gel, sodium alginate, and collagen gel. In this manner, by making the window part 12 from such a nutrient-permeable material and immersing the cell culture vessel 10 in a liquid culture medium, a nutrient, a stimulating factor, and/or the like contained in the liquid culture medium are/is supplied, through the window part 12, to the cell or cell tissue 13 accommodated in the cell culture vessel 10.

Furthermore, by making the window part 12 from a light-transmissive material as described above, it is possible to observe the cell or cell tissue 13 accommodated inside the cell culture vessel 10, from directions of the plurality of faces constituting the cubic shape.

Inside the cell culture vessel 10, the cell or cell tissue 13 and a culture gel 14 which embeds the cell or cell tissue 13 are accommodated. Examples of the culture gel 14 can include collagen, laminin, entactin, and proteoglycan. Further examples of the culture gel 14 can include TGF-β, fibroblast growth factors, and tissue plasminogen activators. Further, for example, Matrigel (registered trademark) can be used for the culture gel 14. The cell or cell tissue 13 accommodated inside the cell culture vessel 10 is three-dimensionally cultured with use of the culture gel 14 as a platform.

The window part 12 is made of a moderately strong material. Thus, it is possible to prevent the window part 12 from being deformed due to the weight of the culture gel 14. Furthermore, a space inside the window part 12 is filled with the culture gel 14 without any gap. Thus, it is possible to prevent the relative position of the embedded cell or cell tissue 13 from being displaced.

Further, in the cell culture vessel 10, only agarose gel that constitutes the window part 12 and an extracellular matrix that constitutes the culture gel 14 interpose between the cell or cell tissue (sample) 13 and the surrounding liquid culture medium. Therefore, circulation of the liquid culture medium and the sample 13 is efficiently carried out. This makes it possible to culture the sample 13 without causing a decrease in activity even in a long-term observation.

The cell culture vessel 10 may include protruding parts 15 which protrude from respective vertices of the frame part 11 toward the inside of the cell culture vessel 10. The protruding parts 15 may be each made entirely of an autofluorescence-emitting material. Alternatively, only end portions 16 of the protruding parts 15 may be each made of an auto-fluorescence-emitting material. In Embodiment 1, the protruding parts 15 each have a triangular pyramid shape, as illustrated in FIG. 1. However, the shapes of the protruding parts 15 and the shapes of the end portions 16 are not particularly limited. The function of the protruding parts 15 will be described below.

When the cell or cell tissue 13 accommodated inside the cell culture vessel 10 is observed from a plurality of directions while the cell culture vessel 10 is being rotated, it is possible to highly accurately align images of the cell or cell tissue 13 which have been obtained from the plurality of directions, by detecting autofluorescence of the protruding parts 15 or the end portions 16.

The protruding parts 15 or the end portions 16 protrude from the respective vertices of the frame part 11 toward the inside of the cell culture vessel 10. Therefore, the protruding parts 15 or the end portions 16 are away from the central part of the cell culture vessel 10, and accordingly do not prevent growth of the embedded cell or cell tissue 13. The protruding parts 15 may be embedded at positions in the culture gel 14 at which the growth of the cell or cell tissue 13 is not prevented.

As illustrated in FIG. 1, the cell culture vessel 10 in accordance with Embodiment 1 includes a shaft part 17 which extends, from any of the vertices of the polyhedral shape, outward in a direction that is not parallel to any of lines normal to the faces of the polyhedral shape.

As an example, the shaft part 17 extends from one vertex V1 of the cell culture vessel 10, which has a cubic shape, in a direction along a straight line 1 connecting the vertex V1 and the vertex V7, which is located at a diagonal position with respect to the vertex V1 (see FIG. 1). Note that a bearing 18 may be provided at the vertex V7, which is located at a diagonal position with respect to the vertex V1.

Alternatively, the shaft part 17 may extend along a straight line which passes through the center of the cell culture vessel 10, as an example. Note, here, that the center of the cell culture vessel 10 refers to, but is not limited to, the center of gravity of the cell culture vessel 10, as an example. For example, the center may refer to an intersection of a plurality of diagonal lines out of diagonal lines connecting the vertices of the cell culture vessel 10 having a polyhedral shape.

The shape of the shaft part 17 is not limited in particular, and may have a rod-like shape, as an example (see FIG. 1). A material of the shaft part 17 may be a non-biocompatible material, provided that the material has a certain degree of strength.

The shaft part 17 may be connected to a rotating mechanism, such as a stepping motor 38, which is capable of rotating the cell culture vessel 10 on the shaft part 17 in a given direction at a given rotational speed. The direction of rotation, the rotational speed, and the duration of the rotation of the stepping motor 38 are controlled by a controller 39. By configuring, as in Embodiment 1, the cell culture vessel 10 such that the cell culture vessel 10 is rotated on the shaft part 17 by a uniaxial rotating mechanism, it is possible to carry out an observation with use of a microscope 40 while rotating the cell culture vessel 10 on the shaft part 17.

Note, however, that in Embodiment 1, instead of the stepping motor 38, an observer may hold the shaft part 17 of the cell culture vessel 10 with use of tweezers or the like and manually rotate the cell culture vessel 10.

As described above, the cell culture vessel 10 in accordance with Embodiment 1 includes the shaft part 17, which extends in the direction that is not parallel to any of the lines normal to the faces of the polyhedral shape constituted by the cell culture vessel 10. Therefore, by manually or automatically rotating the cell culture vessel 10 on the shaft part 17, it is possible to sequentially and three-dimensionally change a face which faces a lens barrel 41 of the microscope 40 illustrated in FIG. 1.

As an example, in a case where the cell culture vessel 10 has a substantially cubic shape as illustrated in FIG. 1, it is possible to, by sequentially rotating the cell culture vessel 10 120 degrees on the shaft part 17, sequentially change a face which faces the lens barrel 41 to the face constituted by V5, V6, V7, and V8 (also referred to as "E face"), the face constituted by V3, V4, V8, and V7 (also referred to as "F face"), and the face constituted by V2, V3, V7, and V6 (also referred to as "D face").

As a result, it is possible to suitably three-dimensionally observe the cell or cell tissue 13 accommodated inside the cell culture vessel 10, by rotating the cell culture vessel 10 on one axis, i.e., the shaft part 17.

<Fixing Tool>

The cell culture vessel 10, which includes the shaft part 17, has been described above. However, a cell culture vessel 10', which does not include a shaft part 17, may be used to observe the cell or cell tissue 13.

Figure 2:
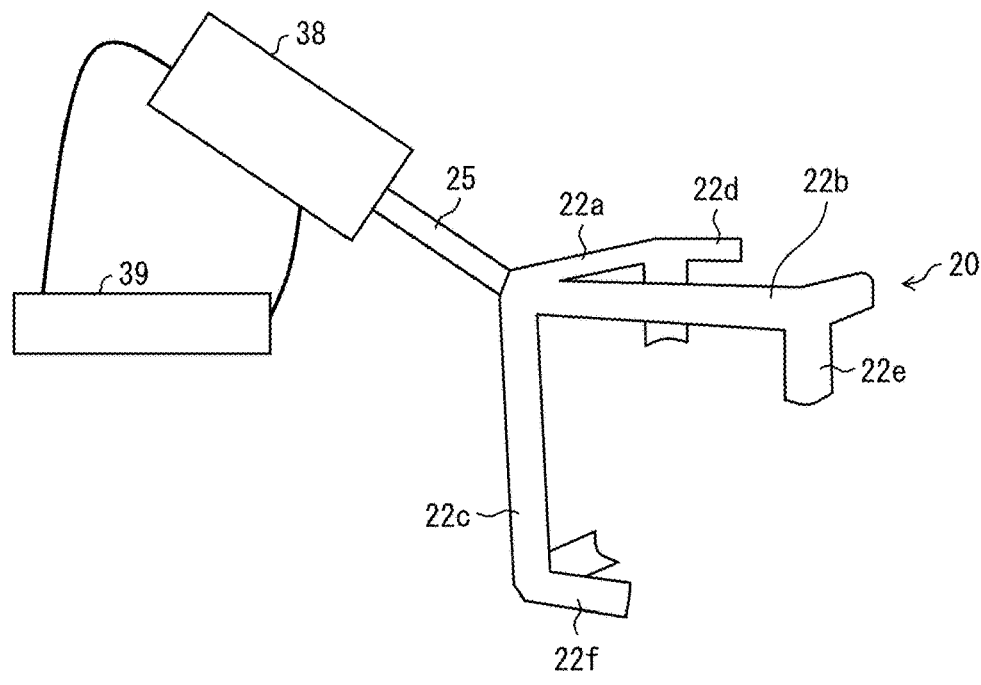
FIG. 2 is a drawing illustrating an example of a fixing tool for fixing the cell culture vessel in accordance with Embodiment 1 of the present invention.
Figure 3:
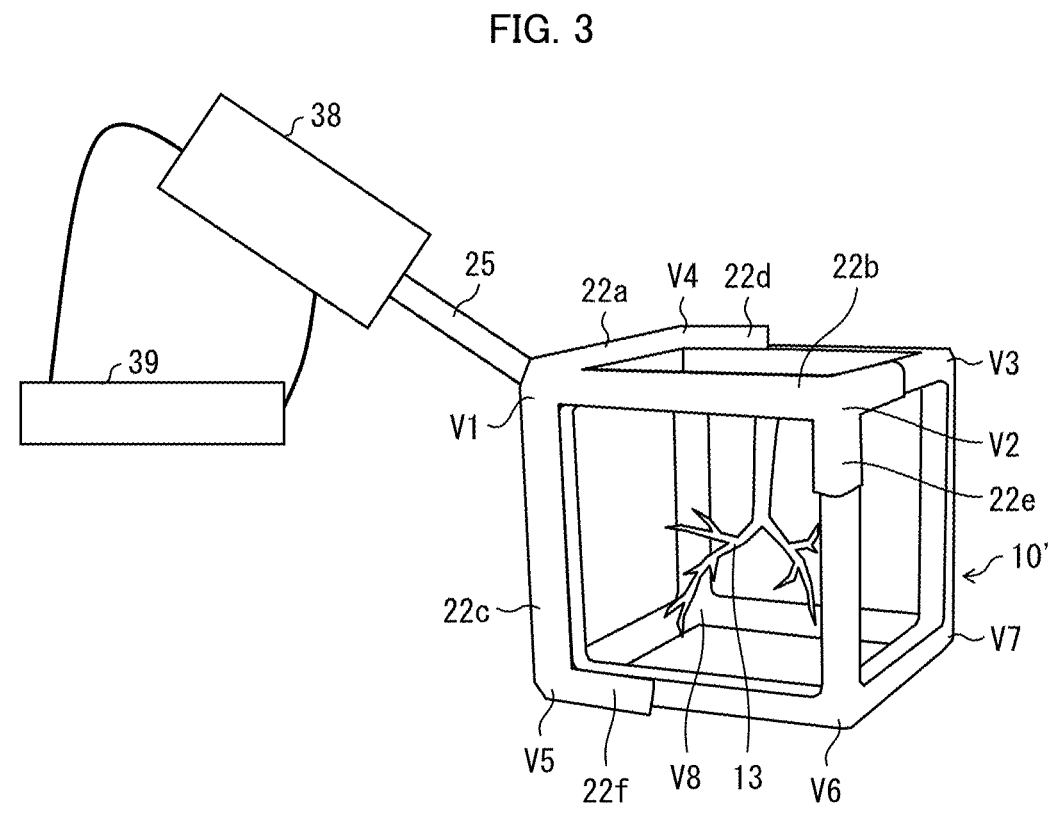

The following description will discuss a fixing tool 20 used to fix the cell culture vessel 10', which does not include a shaft part 17. The cell culture vessel 10' has a configuration similar to that of the above-described cell culture vessel 10, except that the cell culture vessel 10' does not include a shaft part 17. FIG. 2 illustrates an example of the fixing tool 20 used to fix the cell culture vessel 10', which does not include a shaft part 17. FIG. 3 illustrates an example of a state in which the fixing tool 20 is fitted on the cell culture vessel 10'.

As illustrated in FIG. 2, the fixing tool 20 includes a holding part 22 which holds the cell culture vessel 10 and a shaft part 25 which is connected to the holding part 22.

The holding part 22 includes three holding portions 22a, 22b, and 22c which extend in respective directions that form right angles with each other and which have respective substantially equal lengths. The three holding portions 22a, 22b, and 22c have, at ends thereof, claws 22d, 22e, and 22f, respectively.

In a state in which the fixing tool 20 is fitted on the cell culture vessel 10', the holding portions 22a, 22b, and 22c are disposed along respective portions of a frame part 11 which are provided at positions that correspond to respective three sides forming a vertex V1 of the cell culture vessel 10 (a side connecting V1 and V4, a side connecting V1 and V2, and a side connecting V1 and V5), as illustrated in FIG. 3. The claws 22d, 22e, and 22f hold the vertices V4, V2 and V5, respectively, of the frame part which are adjacent to the vertex V1 of the cell culture vessel 10'.

In a state in which the fixing tool 20 is fixed to the cell culture vessel 10', the shaft part 25 of the fixing tool 20 extends, from the vertex V1 of a polyhedral shape (cubic shape) of the cell culture vessel 10', outward in a direction that is not parallel to any of lines normal to faces of the polyhedral shape.

When the cell or cell tissue 13 accommodated in the cell culture vessel 10' is observed, it is possible to obtain images of the cell or cell tissue 13 which have high resolution in a Z-axis direction, as in the case of the cell culture vessel 10 including the shaft part 17, by rotating the cell culture vessel 10' on the shaft part 25 of the fixing tool 20.

<Observation Apparatus and Microscope>

It is possible to obtain time-lapse images of the cell or cell tissue 13, by mounting, on the microscope 40, an observation apparatus 30 which includes (i) the above-described cell culture vessel 10 or the above-described cell culture vessel 10' which is fixed by the fixing tool 20 and (ii) a rotating mechanism. Such an embodiment will be described below.

Figure 4:
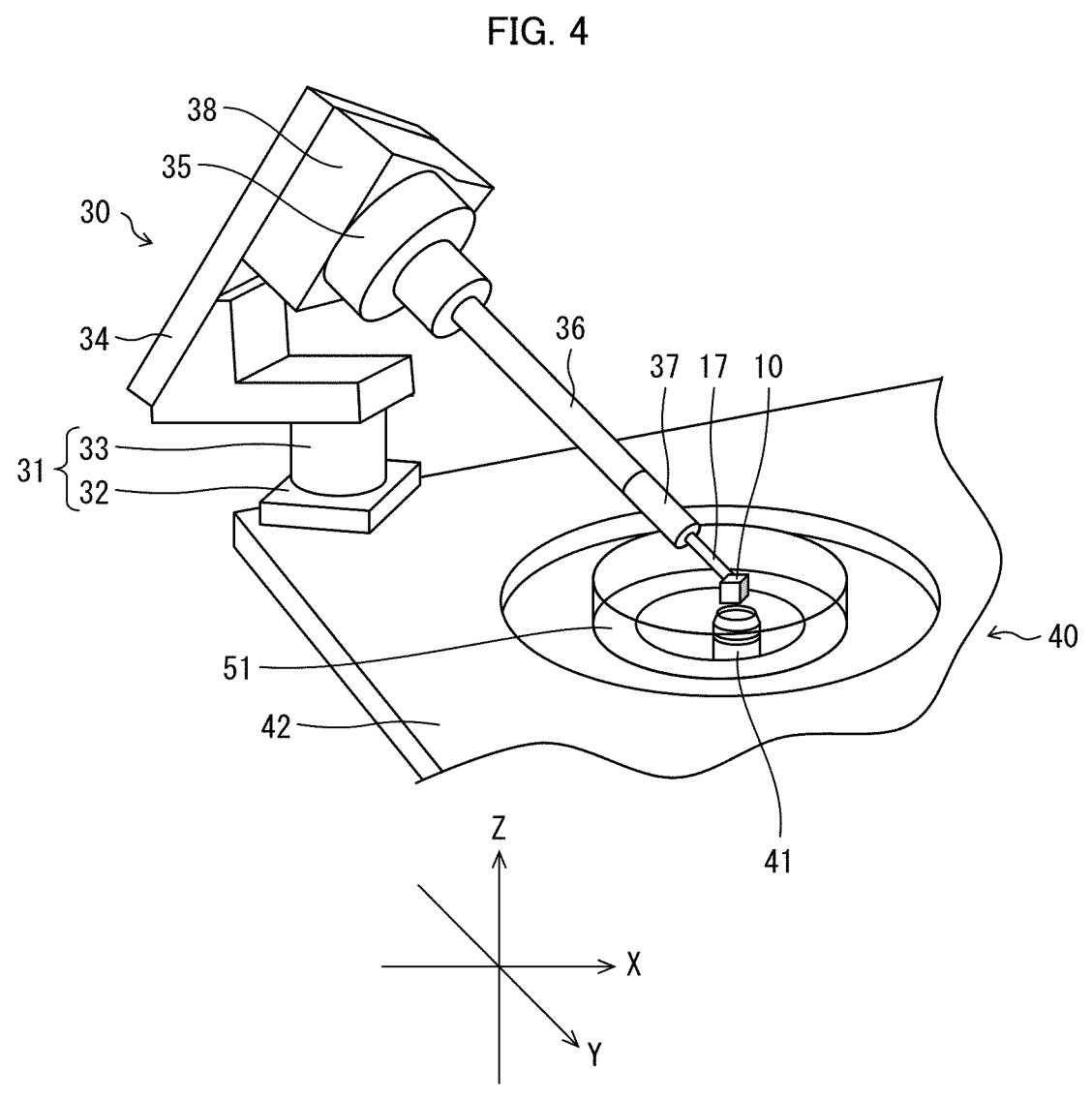

FIG. 4 is a perspective view illustrating a state in which the observation apparatus 30 in accordance with Embodiment 1 of the present invention is mounted on the microscope 40. Coordinate axes illustrated in FIG. 4 are a coordinate system at rest which is expressed by X-, Y-, and Z-axes with the Z-axis as a vertical direction. The following description will discuss the observation apparatus 30 and the microscope 40 on which the observation apparatus 30 is mounted, in accordance with Embodiment 1 of the present invention, with reference to FIG. 4.

The observation apparatus 30 includes (i) the cell culture vessel 10 (or 10', the same applies to the following description) and (ii) a rotating mechanism which holds the shaft part 17 of the cell culture vessel 10 and rotates the cell culture vessel 10 on the shaft part 17.

More specifically, as illustrated in FIG. 4, the observation apparatus 30 in accordance with Embodiment 1 includes a Z-axis mechanical stage 31, an obliquely fixed holder 34, a rotating stage 35, an extending part 36, a collet chuck 37, a stepping motor 38, and the cell culture vessel 10. Note, here, the above rotating mechanism is constituted by, for example, the obliquely fixed holder 34, the extending part 36, the collet chuck 37, and the stepping motor 38.

The observation apparatus 30 in accordance with Embodiment 1 is mounted on a microscope stage 42 of the microscope 40.

The Z-axis mechanical stage 31 of the observation apparatus 30 includes (i) a base 32 which is mounted on the microscope stage 42 of the microscope 40 and (ii) a pedestal part 33 which extends vertically upward with respect to the base 32. The height of the pedestal part 33 in a Z-axis direction can be adjusted. This makes it possible to finely adjust, in the Z-axis direction, the position of the cell culture vessel 10 which is held by the collet chuck 37 (described later).

The obliquely fixed holder 34 is a plate-like member. The obliquely fixed holder 34 is connected to the pedestal part 33 of the Z-axis mechanical stage 31 at an angle with the pedestal part 33. The angle formed by the obliquely fixed holder 34 and the pedestal part 33 of the Z-axis mechanical stage 31 is set such that at least any of lines normal to the faces of the window part included in the cell culture vessel 10 (or 10') can be parallel to the optical axis of the lens barrel 41. For example, in a case where the cell culture vessel 10 (or 10') having a cubic shape is used, the obliquely fixed holder 34 is connected to an upper part of the pedestal part 33 of the Z-axis mechanical stage 31 at an angle of 135 degrees with respect to the pedestal part 33 of the Z-axis mechanical stage 31, as illustrated in FIG. 4. That is, in the embodiment illustrated in FIG. 4, the obliquely fixed holder 34 is fixed to the pedestal part 33 of the Z-axis mechanical stage 31 at an angle of 45 degrees with respect to a horizontal direction (X-Y direction).

To a lower surface of the obliquely fixed holder 34, the rotating stage 35 having a disk shape is provided. The rotating stage 35 is driven by the stepping motor 38 to rotate both clockwise and counterclockwise. By rotating the rotating stage 35, it is possible to rotate, both clockwise and counterclockwise, a member which is attached to an end of the rotating stage 35. Note that the rotating stage 35 may be configured to be rotated automatically with use of the stepping motor 38 or the like as described above or may be alternatively configured to be rotated manually by the observer.

The extending part 36 is connected to the center of the rotating stage 35. The extending part 36 extends linearly in a direction perpendicular to the obliquely fixed holder 34 and the rotating stage 35, i.e., in a direction at an angle of 45 degrees with respect to the horizontal direction (X-Y direction). The collet chuck 37 is connected to an end of the extending part 36. The collet chuck 37 holds the shaft part 17 of the cell culture vessel 10. For example, the collet chuck 37 to which the cell culture vessel 10 is attached may be held at an angle of 45 degrees with respect to a horizontal plane so as to hold the cell culture vessel 10 horizontally. As illustrated in FIG. 4, the cell culture vessel 10 is attached to the collet chuck 37 in a state in which the cell culture vessel 10 is immersed in the liquid culture medium in a dish (or well) 51.

Note that instead of the collet chuck 37 to which the cell culture vessel 10 is attached, the fixing tool 20 which is attached to the cell culture vessel 10', which does not include a shaft part 17, may be attached to the extending part 36.

Thus, by rotating the rotating stage 35, it is possible to rotate the cell culture vessel 10, attached to the end of the collet chuck 37, on the shaft part 17 at a given speed, while keeping the extending part 36 at an angle of 45 degrees with respect to the horizontal direction. The rotational speed and the duration of rotation of the rotating stage 35 (i.e., the rotational speed, the stopping time, and the duration of rotation of the cell culture vessel 10) can be set arbitrarily. This enables (i) continuous rotation and also (ii) an intermittent operation in which rotation and a stop are repeated. For example, the rotational speed may be set such that the cell culture vessel 10 is rotated clockwise twice per minute (i.e., rotated 120 degrees in 10 seconds), and the duration of the rotation may be set to three days, during which a cycle in which (i) after the cell culture vessel 10 has been rotated 120 degrees, the rotation of the cell culture vessel 10 is stopped for 110 seconds and then (ii) the cell culture vessel 10 is rotated again clockwise 120 degrees is repeated.

<Observation of Cell or Cell Tissue with Microscope>

The following description will discuss a method of (i) setting, in the microscope 40, the cell culture vessel 10 in a state of being immersed in the liquid culture medium and being connected to the observation apparatus 30 and (ii) carrying out an observation. As the microscope 40, a microscope conventionally used can be used. For example, a confocal laser scanning microscope or a two-photon microscope can be used as the microscope 40. Note that FIG. 4 illustrates an inverted microscope as an example, but the microscope 40 may be an upright microscope.

As illustrated in FIG. 4, the cell culture vessel 10 is immersed in the liquid culture medium in the dish (or well) 51.

In a case where the cell culture vessel 10 is observed, the cell culture vessel 10 in a state of being immersed in the dish 51 is placed on the microscope stage 42 so that the cell or cell tissue 13 accommodated in the cell culture vessel 10 is located within the field of view of the lens barrel 41 of the microscope 40.

The Z-axis mechanical stage 31 of the observation apparatus 30 is then mounted at a given position on the microscope stage 42 of the microscope 40. Subsequently, the cell culture vessel 10 in the state of being horizontally immersed in the dish 51 is connected to the end of the extending part 36 of the observation apparatus 30 via the collet chuck 37. Thereafter, the position in the Z-axis direction at which the cell culture vessel 10 is set is finely adjusted with use of the Z-axis mechanical stage 31.

When the position of the cell culture vessel 10 is determined, the rotational speed, the stopping time in the intermittent operation, and the duration of the rotation of the rotating stage 35 are set. Observing the cell or cell tissue 13 (i.e., obtaining images) while the rotation is being stopped is repeated.

<Rotation of Cell Culture Vessel>

Figure 5:
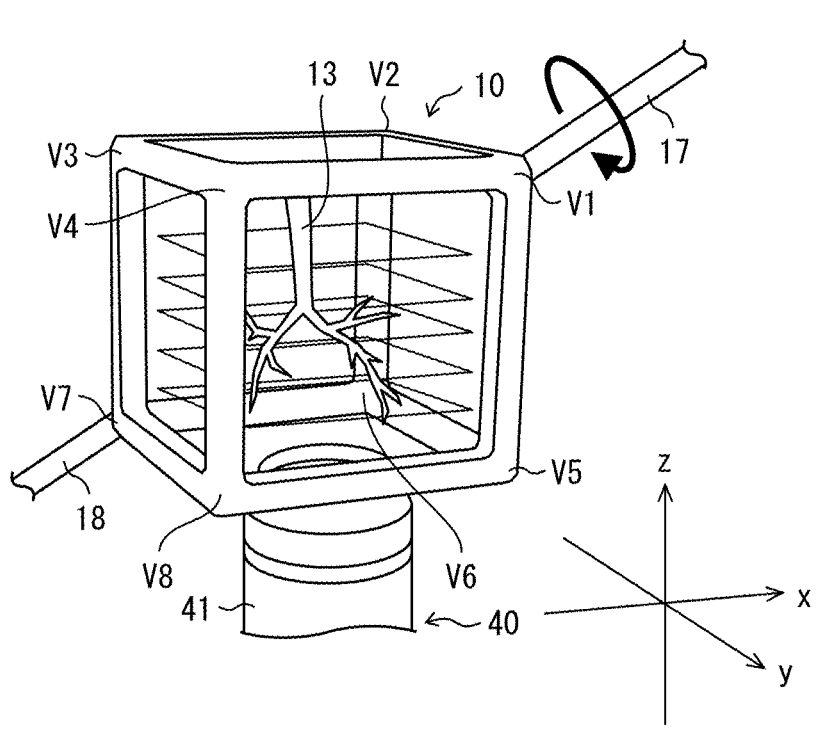
FIG. 5 is a drawing illustrating rotation of the cell culture vessel in accordance with Embodiment 1 of the present invention.
Figure 6:
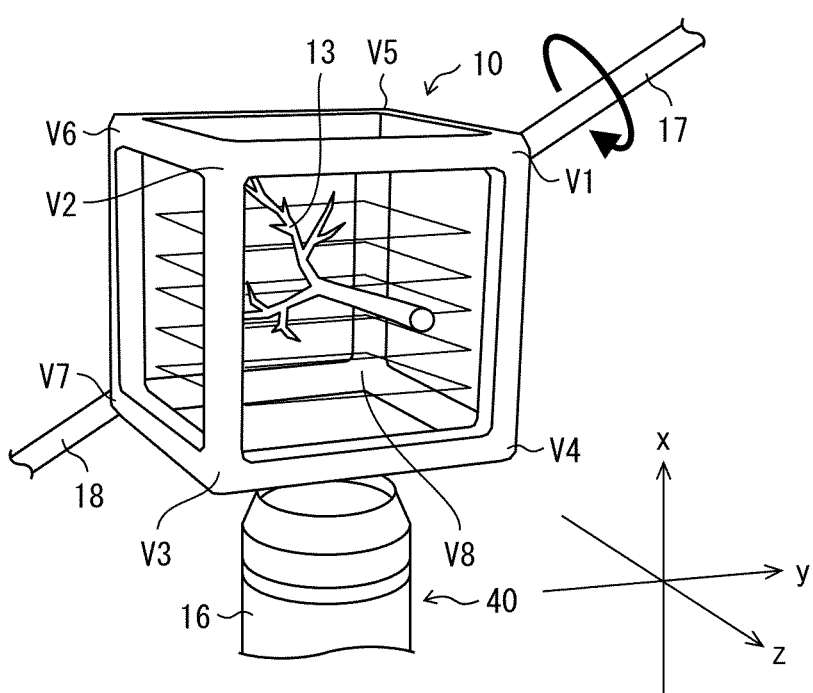
FIG. 6 is a drawing illustrating rotation of the cell culture vessel in accordance with Embodiment 1 of the present invention.
Figure 7:
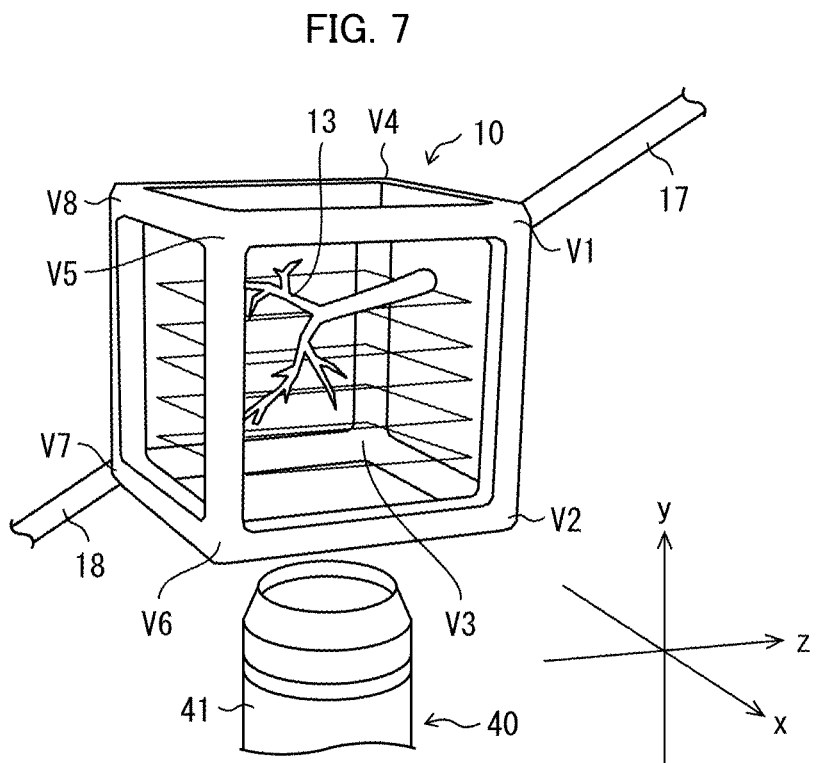
FIG. 7 is a drawing illustrating rotation of the cell culture vessel in accordance with Embodiment 1 of the present invention.

FIGS. 5 to 7 each illustrate rotation of the cell culture vessel 10 during an operation of observing the cell or cell tissue 13. A coordinate system illustrated in each of FIGS. 5 to 7 is a local coordinate system which is expressed by x-, y-, and z-axes and which is associated with the cell culture vessel 10. In Embodiment 1, setting is carried out such that the cell culture vessel 10 is rotated clockwise 120 degrees on the shaft part 17 every 2 minutes and this rotation lasts for 3 days.

As illustrated in FIG. 5, at a start of obtainment of images, an A face (face constituted by the vertices V1, V4, V8, and V5), out of the six faces constituting the cubic shape of the cell culture vessel 10, is located in the foreground, and the E face (face constituted by the vertices V5, V6, V7, and V8) faces the lens barrel 41. At this time, images of the sample 13 can be obtained by scanning the sample 13 in the z-axis direction of the cell culture vessel 10.

Subsequently, when the cell culture vessel 10 is rotated clockwise 120 degrees on the shaft part 17, a B face (face constituted by the vertices V2, V3, V4, and V1) is located in the foreground, and the F face (face constituted by the vertices V3, V4, V8, and V7) faces the lens barrel 41, as illustrated in FIG. 6. At this time, images of the sample 13 can be obtained by scanning the sample 13 in an x-axis direction of the cell culture vessel 10.

When the cell culture vessel 10 is further rotated clockwise 120 degrees on the shaft part 17, a C face (face constituted by the vertices V1, V4, V8, and V5) is located in the foreground, and the D face (face constituted by the vertices V2, V3, V7, and V6) faces the lens barrel 41, as illustrated in FIG. 7. At this time, images of the sample 13 can be obtained by scanning the sample 13 in a y-axis direction of the cell culture vessel 10.

When the cell culture vessel 10 is further rotated clockwise 120 degrees on the shaft part 17, the cell culture vessel 10 returns to a state in which the A face is located in the foreground, as illustrated in FIG. 5. The same operation is repeated thereafter.

Namely, each time the cell culture vessel 10 is rotated clockwise 120 degrees on the shaft part 17, the A face, the B face, and the C face, which are three faces forming the vertex V1 of the cell culture vessel 10 that is the origin of extension of the shaft part 17, are sequentially located in the foreground.

As a result, it is possible to sequentially obtain images of the sample 13 which show the sample 13 that is sliced in the x-y direction, the y-z direction, and a z-x plane of the cell culture vessel 10, by scanning the sample 13 in the z-axis direction, the x-axis direction, and the y-axis direction, respectively, of the cell culture vessel 10. By synthesizing these pieces of image data obtained from the plurality of faces, it is possible to obtain a three-dimensional structure of the sample 13 with high resolution in all of the x-axis direction, the y-axis direction, and the z-axis direction.

<Observation Result>

In Embodiment 1, an observation was carried out with use of zebrafish as the sample 13. The cell culture vessel 10 in which the zebrafish was accommodated and which was in a state of being immersed in the dish 51 was set at a given position in the microscope 40, and the cell culture vessel 10 was rotated by the stepping motor 38. At this time, the rotational speed was set such that the cell culture vessel 10 was rotated twice per minute (i.e., rotated 120 degrees in 10 seconds), and an operation of repeating a cycle in which (i) after the cell culture vessel 10 had been rotated 120 degrees, the rotation of the cell culture vessel 10 was stopped for 110 seconds and then (ii) the cell culture vessel 10 was rotated again clockwise 120 degrees was set to be carried out for 3 days. Images of the zebrafish were obtained by scanning the zebrafish in the axial direction of the lens barrel 41, while rotation carried out every 2 minutes was stopped. The following description will discuss images of cell tissue which were obtained with use of the observation apparatus 30 in accordance with Embodiment 1, with reference to FIGS. 8 and 9.

Figure 8:
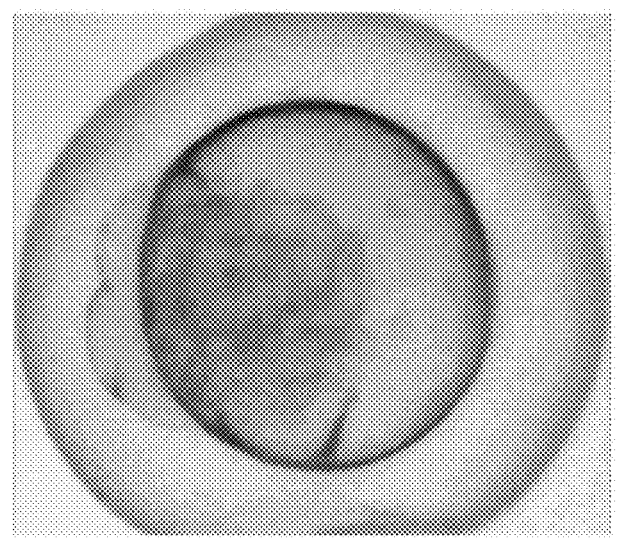
FIG. 8 shows examples of images of cell tissue which were obtained at certain times by the observation apparatus in accordance with Embodiment 1 of the present invention (images obtained by observing the cell tissue from an x-y direction, a y-z direction, and an x-y direction in a local coordinate system of the cell culture vessel).
Figure 8:
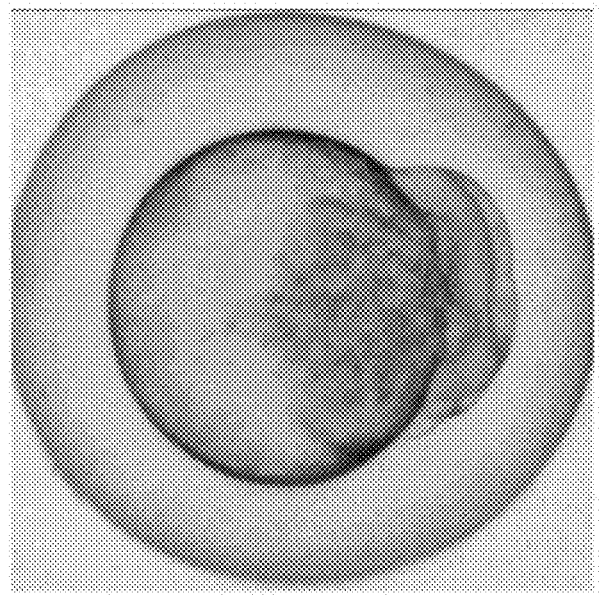
Figure 8:
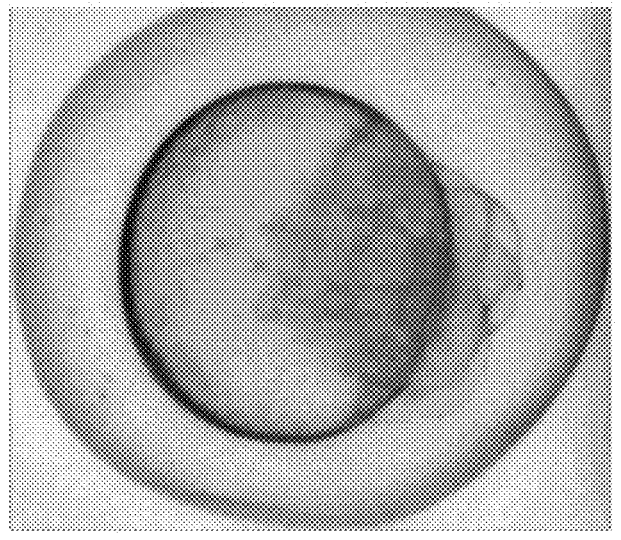
Figure 9:
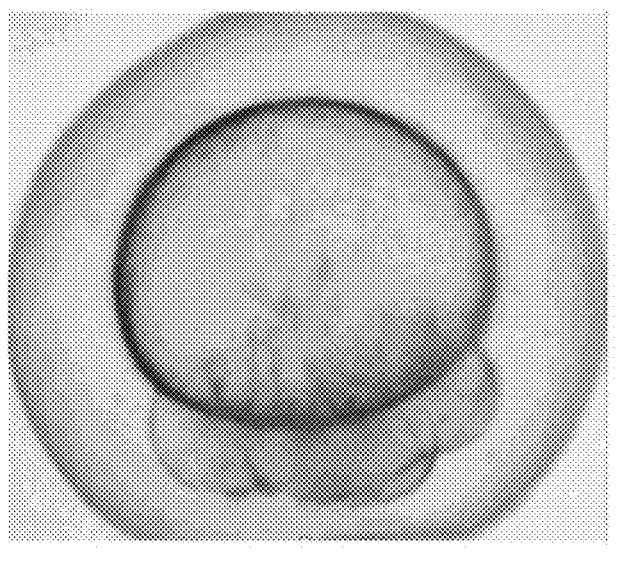
FIG. 9 shows examples of images of the cell tissue which were obtained at the other times by the observation apparatus in accordance with Embodiment 1 of the present invention (images obtained by observing the cell tissue from the x-y direction, the y-z direction, and the x-y direction in the local coordinate system of the cell culture vessel).
Figure 9:
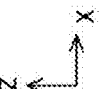
Figure 9:
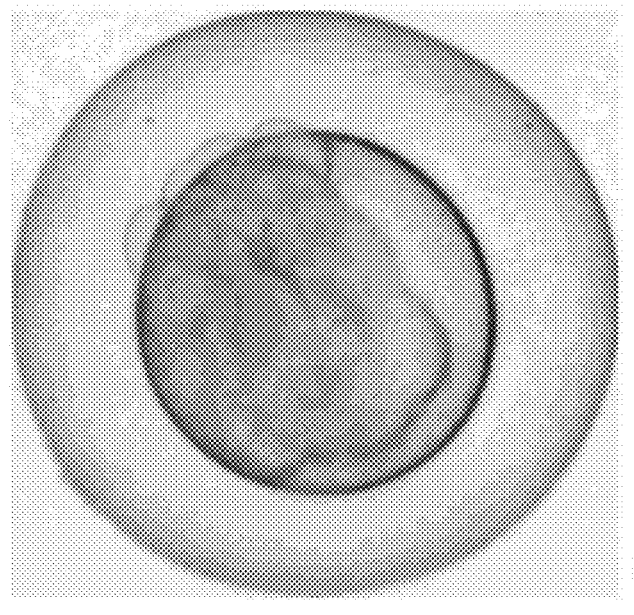
Figure 9:
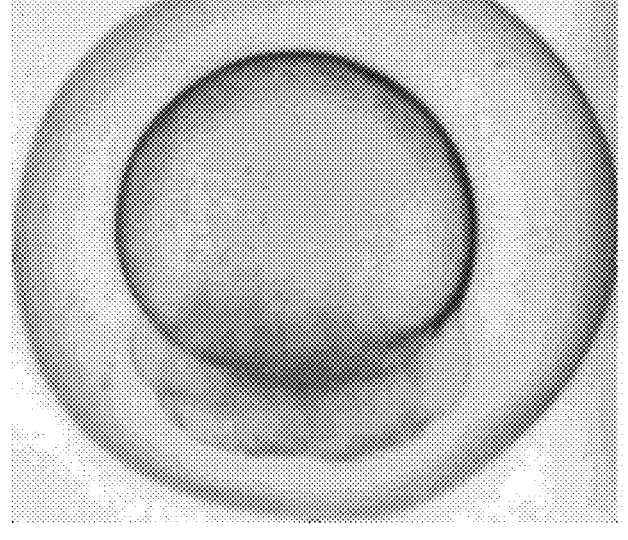

Three images shown in FIG. 8 are a projection image of the zebrafish in the x-y direction at a certain time t1, a projection image of the zebrafish in the y-z direction at a time t2, which was two 2 minutes after the time t1, and a projection image of the zebrafish in the z-x direction at a time t3, which was 2 minutes after the time t2. Three images shown in FIG. 9 are an image of the zebrafish in the x-y direction at a time t4, which was 2 minutes after the time t3, an image of the zebrafish in the y-z direction at a time t5, which was 2 minutes after the time t4, and an image of the zebrafish in the z-x direction at a time t6, which was 2 minutes after the time t5. In this manner, the cell culture vessel 10 in which the zebrafish was accommodated continued to be rotated clockwise 120 degrees every 2 minutes for 3 days. During this operation, it was possible to successively obtain images of the zebrafish in the x-y direction, the y-z direction, and the z-x direction every 2 minutes.

As described above, by successively obtaining images of the sample 13 at regular intervals while automatically rotating the cell culture vessel 10 in accordance with Embodiment 1 of the present invention with use of the stepping motor 38 or the like, it is possible to carry out time-lapse measurement of the sample 13 (zebrafish in Embodiment 1), and possible to carry out a live observation of a intracellular kinetics with use of the observation apparatus 30.

Note that, in Embodiment 1, the observation apparatus 30 is separate from the microscope 40, but the microscope 40 may include the observation apparatus 30 having the above configuration.

Embodiment 2

The following description will discuss Embodiment 2 of the present invention. For convenience, members having the same functions as those of the members described in Embodiment 1 are denoted by the same reference numerals, and description thereof will not be repeated.

In Embodiment 1, an example has been described in which the sample (cell or cell tissue) 13 is observed with use of the microscope 40 which is of such a type that the sample

13 is observed while light is being emitted to the sample 13 from one direction. However, the present invention is not limited to a microscope having such a configuration, and can be applied to all types of microscopes.

Figure 10:
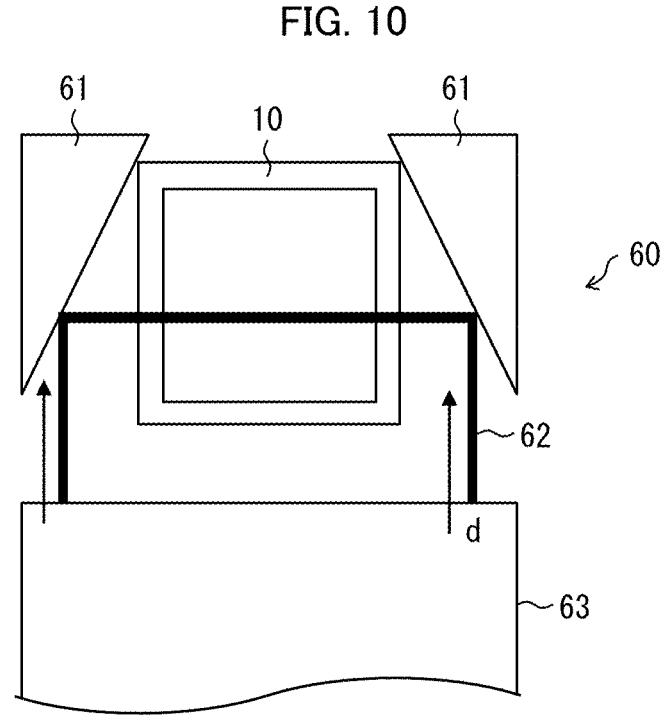
FIG. 10 is a drawing for explaining the principles of a microscope in accordance with Embodiment 2 of the present invention.

For example, the present invention can be also applied to a light-sheet microscope 60 as illustrated in FIG. 10. In the light-sheet microscope 60 illustrated in FIG. 10, lasers from a laser emitting section 63 which is disposed below a cell culture vessel 10 are reflected by respective two mirrors 61, and sheet-like lasers (light sheets 62) are emitted from respective two opposite sides of the cell culture vessel 10 in which a cell or cell tissue, which is a sample 13, is accommodated. Then, by scanning the sample 13 in a direction perpendicular to the light sheets 62, images of the sample 13 are obtained. Therefore, for example, by (i) mounting, on the light-sheet microscope 60, an observation apparatus 30 which includes the cell culture vessel 10 having a cubic shape as has been described above and (ii) observing the sample 13, it is possible to observe the sample 13 from all of directions of six faces of the cell culture vessel 10 forming a cube. Thus, it is possible to obtain a three-dimensional image of a target of an observation which has higher resolution.

Note that the light-sheet microscope in accordance with Embodiment 2 is not limited to a configuration illustrated in FIG. 10. For example, the light-sheet microscope 60 may be configured not to include the two mirrors 61, and configured such that a sheet-like laser is emitted from a laser emitting section disposed on a side of the cell culture vessel 10.

Embodiment 3

In Embodiment 1, the observation apparatus which is used to observe a biological cell or biological cell tissue, such as zebrafish, that can be cultured without strict control of a culture condition has been described. In contrast, in Embodiment 3, an observation apparatus 130 is used which enables an observation of a cell or cell tissue that requires strict control of a culture condition, such as a temperature or a $CO_2$ (carbon dioxide) concentration, around the cell or cell tissue. For example, in the case of a normal human bronchial epithelial cell (NHBE), culture conditions are desirably such that a temperature around the cell or cell tissue is maintained at 36° C. to 37° C. and a $CO_2$ concentration around the cell or cell tissue is maintained in a range of 4.0% to 5.0%, and are, in particular, most desirably such that the temperature around the cell or cell tissue is maintained at 37° C. and the $CO_2$ concentration around the cell or cell tissue is maintained at approximately 5%. By maintaining the temperature around the cell or cell tissue at 37° C., which is comparable to a body temperature, it is possible to cause the activity of an enzyme which is added to a culture medium to be active. Further, by maintaining the $CO_2$ concentration at approximately 5%, it is possible to maintain a pH of the culture medium at a neutral (7.2 to 7.4).

<Configuration of Observation Apparatus>

A configuration of the observation apparatus 130 in accordance with Embodiment 3 will be described with reference to FIGS. 11 to 14. Note, however, that only differences from the observation apparatus 13 described in Embodiment 1 will be described, and members having similar configurations are denoted by the same reference numerals, and descriptions thereof will be omitted.

Figure 11:
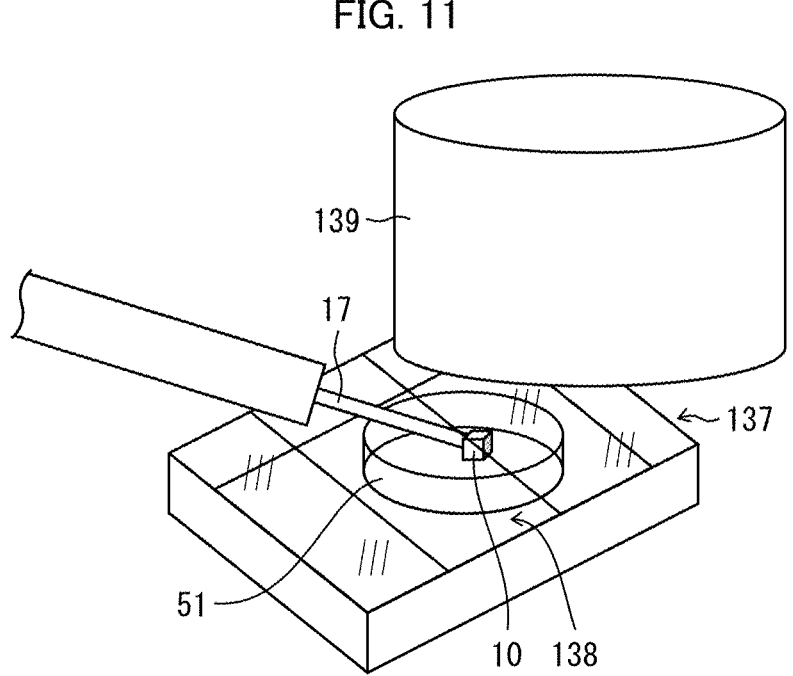
FIG. 11 is a perspective view illustrating an example of an observation apparatus in accordance with Embodiment 3 of the present invention, and illustrating a state in which a cell culture vessel is accommodated in a chamber.
Figures 12, 13:
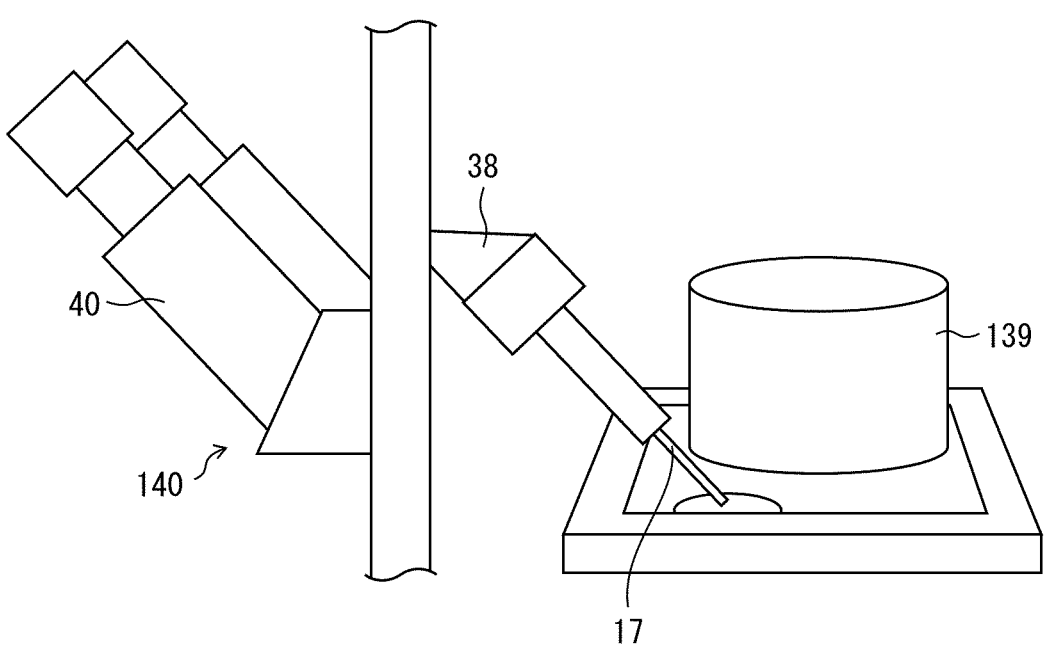
FIG. 12 is a drawing illustrating a state in which, in the observation apparatus illustrated in FIG. 11, the cell culture vessel is sealed in the chamber after the cell culture vessel has been accommodated in the chamber.
FIG. 13 is a block diagram illustrating an example of a hardware configuration of the observation apparatus in accordance with Embodiment 3 of the present invention.
Figure 14:
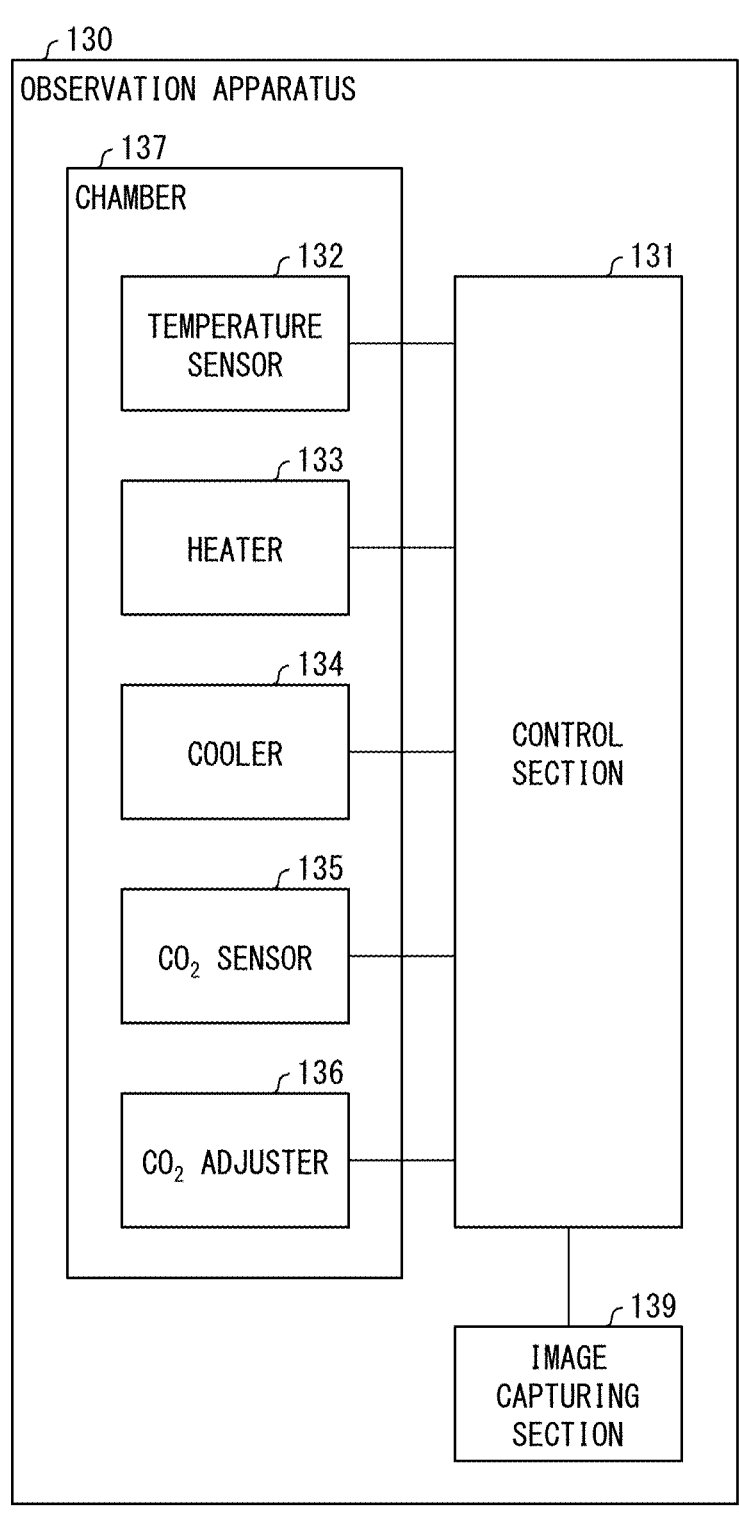
FIG. 14 illustrates the observation apparatus in accordance with Embodiment 3 of the present invention.

FIG. 11 is a perspective view illustrating an example of the observation apparatus 130 in accordance with Embodiment 3, and illustrating a state in which a cell culture vessel 10 is accommodated in a chamber 137 of the observation apparatus 130. FIG. 12 is a drawing illustrating a state in which, in the observation apparatus 130 illustrated in FIG. 11, the cell culture vessel 10 is sealed in the chamber 137 after the cell culture vessel 10 has been accommodated in a dish 51. FIG. 13 is a drawing illustrating an example of a three-axis adjusting mechanism 140 which adjusts the position of the observation apparatus 130 in accordance with Embodiment 3 of the present invention. FIG. 14 is a block diagram illustrating a hardware configuration of the observation apparatus 130.

The observation apparatus 130 further includes, in addition to the constituent elements included in the observation apparatus 30 in Embodiment 1, (i) the chamber 137 in which the culture vessel 10 (in which a normal human bronchial epithelial cell is cultured) is accommodated and (ii) a control section 131 which controls a culture condition in the chamber 137. As illustrated in FIG. 14, the observation apparatus 130 further includes a temperature sensor 132, a heater 133, a cooler 134, a $CO_2$ concentration sensor 135, and a $CO_2$ adjuster 136. As illustrated in FIG. 11, the chamber 137 is mounted at a given position on a microscope stage 42.

Note, here, that in order that the chamber 137 is mounted at the given position on the microscope stage 42, a microscope includes the three-axis adjusting mechanism 140 as illustrated in FIG. 13. The three-axis adjusting mechanism 140 is connected to a stepping motor 38 of the observation apparatus 130, and is capable of moving the observation apparatus 130 in a y-axis direction, a z-axis direction, and a direction which is at 45 degrees with respect to the z-axis direction and which is perpendicular to a y axis (i.e., a direction parallel to a shaft part 17 of the cell culture vessel).

To an end of the shaft part 17 of the observation apparatus 130, the culture vessel 10 in a state of being immersed in a liquid culture medium in the dish (or well) 51 is attached. The control section 131 controls the culture vessel 10, which is attached to the end of the shaft part 17 of the observation apparatus 130, so that the culture vessel 10 is accommodated in the chamber 137 through a slit 138, as illustrated in FIG. 11. Note, however, that a human may manually accommodate the culture vessel 10 in the chamber 137. The control section 131 controls the chamber 137 so that the chamber 137 is sealed, after the culture vessel 10 has been accommodated in the chamber 137. By sealing the chamber 137, it is possible to strictly control the culture condition in the chamber 137. For the dish (or well) 51, silicone oil is used to prevent evaporation from a surface of the liquid culture medium.

<Adjustment of Culture Condition>

The control section 131 controls the culture condition around the cell in the chamber, under which the cell is cultured, or the culture condition around the cell tissue in the chamber, under which the cell tissue is cultured. For example, the control section 131 controls at least one of the temperature and $CO_2$ (carbon dioxide concentration) around the cell or at least one of the temperature and the $CO_2$ concentration around the cell tissue. The observation apparatus 130 further includes the heater 133, the cooler 134, the temperature sensor 132, the $CO_2$ concentration sensor 135, and the $CO_2$ adjuster 136.

The control section 131 controls the temperature around the normal human bronchial epithelial cell so that the temperature is maintained at 36° C. to 37° C. In particular, the control section 131 preferably controls the temperature around the normal human bronchial epithelial cell so that the temperature is maintained at 37° C. The heater 133 and the cooler 134 are provided to a surface of a top plate or a bottom plate of the observation apparatus 130. The control section 131 controls, on the basis of the temperature measured by the temperature sensor 132, the heater 133 or the cooler 134 so that the heater 133 or the cooler 134 is switched on or off and accordingly the temperature around the cell or cell tissue is maintained in an appropriate temperature range. For example, setting may be carried out such that, in a case where a result of measurement carried out by the temperature sensor 132 is not higher than 36° C., the control section 131 controls the heater 133 so that the heater 133 is switched on and, in a case where the result of the measurement carried out by the temperature sensor 132 is not lower than 37° C., the control section 131 controls the cooler 134 so that the cooler 134 is switched on.

The control section 131 controls the $CO_2$ concentration around the normal human bronchial epithelial cell so that the $CO_2$ concentration is maintained at 4.0% to 5.0%. Most preferably, the control section 131 controls the $CO_2$ concentration around the cell or cell tissue so that the $CO_2$ concentration is maintained at 5%. As the $CO_2$ concentration sensor, a known $CO_2$ concentration sensor, such as an optical $CO_2$ concentration sensor, an electrochemical $CO_2$ concentration sensor, or a semiconductive $CO_2$ concentration sensor, can be used. The control section 131 may be configured to control the $CO_2$ adjuster 136 so that the $CO_2$ adjuster 136 is operated and accordingly the $CO_2$ concentration is adjusted, in a case where the $CO_2$ concentration exceeds an appropriate range. Instead of the $CO_2$ concentration, the pH of the culture medium may be adjusted. For example, control may be carried out so that, in a case where the pH exceeds a range of 7.2 to 7.4, the $CO_2$ adjuster 136 adjusts the $CO_2$ concentration and consequently the pH of the culture medium is adjusted to an appropriate range. Alternatively, the culture medium may be caused to contain phenol red, and a human may determine the pH by a change in color of the culture medium.

In this manner, by using the observation apparatus 130 in accordance with Embodiment 3 to maintain, in respective appropriate ranges, the temperature and the $CO_2$ concentration around the cell or cell tissue to be cultured, it is possible to appropriately culture and observe over time the normal human bronchial epithelial cell. The observation apparatus 130 in accordance with Embodiment 3 can be also applied to culture and an over-time observation of the other cells or cell tissue which require strict culture conditions. Depending on the types of the cells or cell tissue, it is possible to appropriately set temperatures and $CO_2$ concentrations. For example, the control section 131 may be configured to (i) receive information on the type of the cell or cell tissue which is a target of an observation and (ii) set the temperature or the carbon dioxide concentration in accordance with the information.

Furthermore, a groove-like space may be provided in the chamber 137, and pure water may be constantly put in the space so that the humidity in the chamber 137 is maintained at 90% to 98%. According to the above configuration, it is possible to prevent evaporation from the culture medium in the dish 51, and possible to carry out a long-term time-lapse observation.

<Culture and Observation>

As described above, FIG. 12 illustrates a state in which the chamber 137 is closed after the observation apparatus 130 has been set in the chamber 137.

In this state, a normal human bronchial epithelial cell was cultured while a temperature was being maintained at 37° C. and a $CO_2$ concentration was being maintained at 5%. Simultaneously, in the same manner as in Embodiment 1, the culture vessel 10 was rotated, and images were obtained by successively scanning the normal human bronchial epithelial cell from directions of three faces with use of an image capturing section 139. The normal human bronchial epithelial cell was labeled with green fluorescent protein (GFP). In Embodiment 3, the culture vessel 10 was rotated 120 degrees every 4 minutes, and the cell was three-dimensionally tracked from the directions of the three faces.

Figure 15:
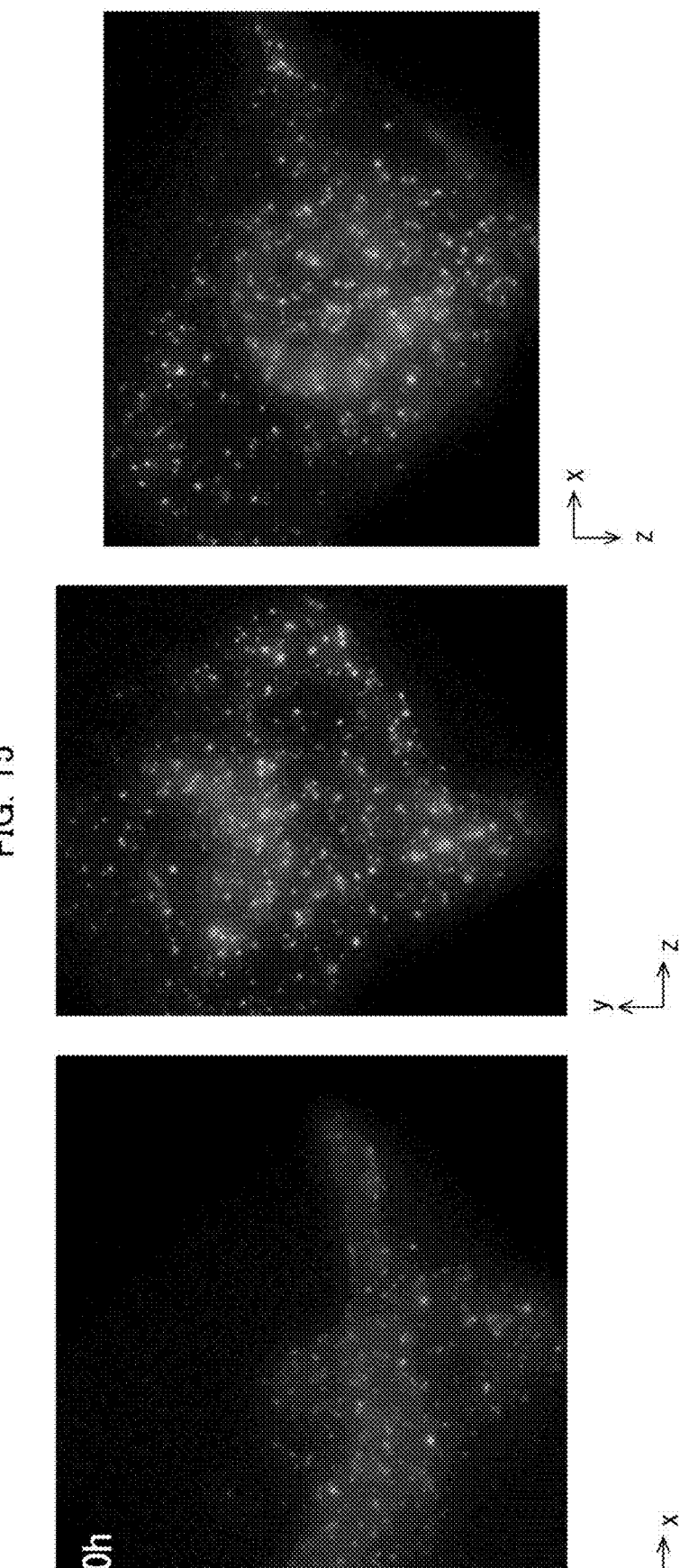
FIG. 15 shows examples of images of cell tissue which were obtained at certain times by the observation apparatus in accordance with Embodiment 3 of the present invention (images obtained by observing the cell tissue from an x-y direction, a y-z direction, and an x-y direction in a local coordinate system of the cell culture vessel).
Figure 16:
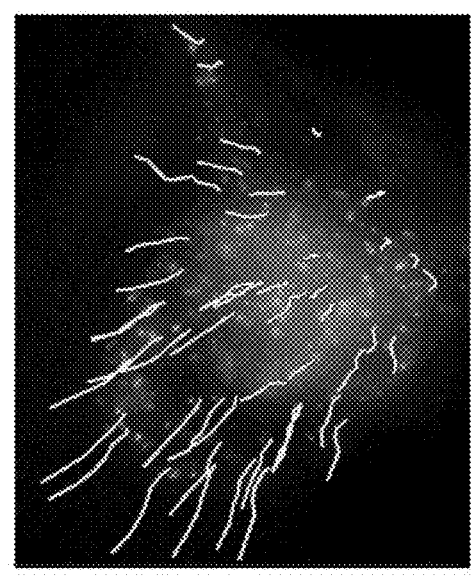
FIG. 16 shows images obtained by overlapping trajectories of the cell tissue on images which were of the cell tissue illustrated in FIG. 15 and which were captured 7 hours later.
Figure 16:
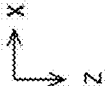
Figure 16:
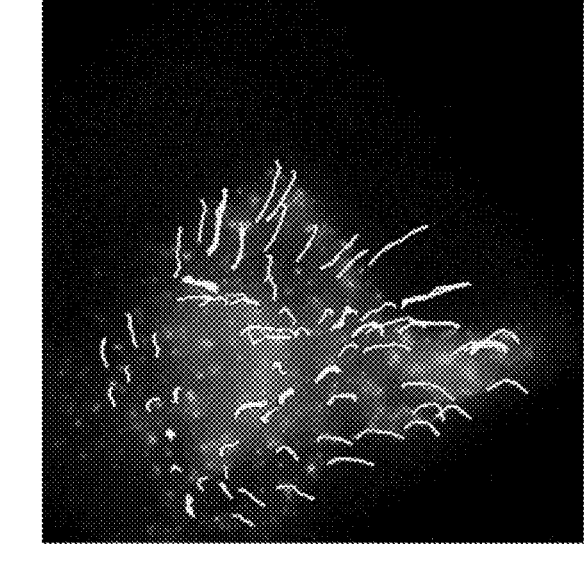
Figure 16:
Figure 16:
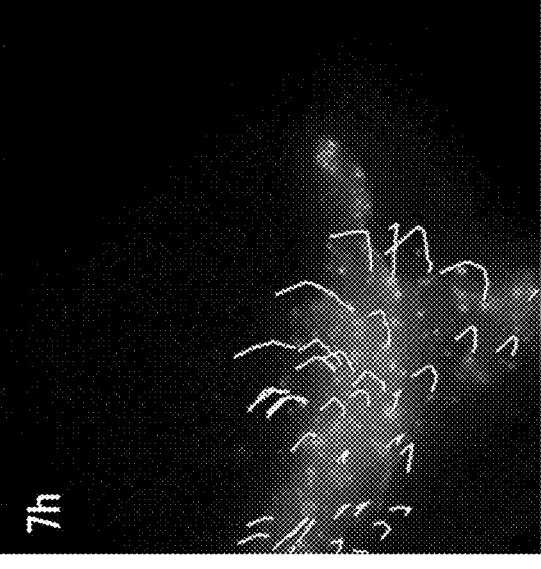
Figure 16:

FIG. 15 shows examples of images of the normal human bronchial epithelial cell which were obtained at certain times as a result of the above operation (images obtained by observing the normal human bronchial epithelial cell from an x-y direction, a y-z direction, and an x-y direction in a local coordinate system of the cell culture vessel 10). Specifically, FIG. 15-1 is an image of the cell tissue which was captured from the z-axis direction, FIG. 15-2 is an image of the cell tissue which was captured from the y-axis direction, and FIG. 15-3 is an image of the cell tissue which was captured from the x-axis direction. FIG. 16 shows images obtained by overlapping trajectories of the cell tissue on images which were of the cell tissue illustrated in FIG. 15 and which were captured 7 hours later. Specifically, FIG. 16-1 is an image of the cell tissue which was captured from the z-axis direction, FIG. 16-2 is an image of the cell tissue which was captured from the y-axis direction, and FIG. 16-3 is an image of the cell tissue which was captured from the x-axis direction.

In this manner, with use of the observation apparatus 130 in accordance with Embodiment 3, it is possible to observe, over time, even a cell or cell tissue which requires strict control of a culture condition, such as a normal human bronchial epithelial cell.

Aspects of the present invention can also be expressed as follows:

[First Aspect]

A cell culture vessel 10 in accordance with a first aspect of the present invention is a cell culture vessel for accommodating a cell or cell tissue therein, including: a frame part 11 which is provided so as to be located at positions that correspond to respective sides of a polyhedral shape; a window part 12 which is light-transmissive and which is provided so as to be located at positions that correspond to a respective plurality of faces out of faces of the polyhedral shape; and a shaft part 17 which extends, from any of vertices of the polyhedral shape, outward in a direction that is not parallel to any of lines normal to the faces of the polyhedral shape.

According to the above configuration, it is possible to reduce a burden on an observer. For example, use of the cell culture vessel makes it possible to obtain suitable observation images while suppressing a burden on an observer, by observing, from a plurality of directions, a cell or cell tissue accommodated in the cell culture vessel while rotating the cell culture vessel on the shaft part.

[Second Aspect]

The cell culture vessel in accordance with a second aspect of the present invention may be arranged such that, in the first aspect, the shaft part extends along a straight line that passes through the any of the vertices and a center of the cell culture vessel.

According to the above configuration, it is possible to obtain a plurality of images which are not displaced in a z-axis direction, by observing a cell or cell tissue from a plurality of directions while rotating the cell culture vessel on the shaft part in a state in which the center point of the cell culture vessel is fixed. By interpolation between these pieces of image data, it is possible to further obtain a highly accurate image of the cell tissue.

[Third Aspect]

The cell culture vessel in accordance with a third aspect of the present invention may be arranged such that, in the first or second aspect, the polyhedral shape is a hexahedral shape.

According to the above configuration, it is possible to obtain a plurality of images from direction of three faces which form the vertex that is the origin of extension of the shaft part, by rotating the cell culture vessel on the shaft part. By interpolation between these images, it is possible to obtain a highly accurate image of the cell tissue.

[Fourth Aspect]

An observation apparatus in accordance with a fourth aspect of the present invention is an observation apparatus including a rotating mechanism which holds a shaft part of a cell culture vessel and which rotates the cell culture vessel on the shaft part, the cell culture vessel being for accommodating a cell or cell tissue therein, the cell culture vessel including: a frame part which is provided so as to be located at positions that correspond to respective sides of a polyhedral shape; a window part which is light-transmissive and which is provided so as to be located at positions that correspond to a respective plurality of faces out of faces of the polyhedral shape; and the shaft part which extends, from any of vertices of the polyhedral shape, outward in a direction that is not parallel to any of lines normal to the faces of the polyhedral shape. According to the above configuration, it is possible to suitably carry out an observation with use of the cell culture vessel.

[Fifth Aspect]

The observation apparatus in accordance with a fifth aspect of the present invention is arranged so as to further include: a chamber in which the cell culture vessel is accommodated; and a control section which controls a culture condition around the cell or the cell tissue in the chamber, under which the cell or the cell tissue is cultured. According to the above configuration, it is possible to suitably observe, over time, even a cell which requires strict control of a culture condition, such as a normal human bronchial epithelial cell, with use of the cell culture vessel.

[Sixth Aspect]

The observation apparatus in accordance with a sixth aspect of the present invention is arranged such that the control section controls at least one of a temperature and a $CO_2$ concentration around the cell or the cell tissue. According to the above configuration, it is possible to suitably observe, over time, even a cell which requires strict control of a culture condition, such as a normal human bronchial epithelial cell, with use of the cell culture vessel.

[Seventh Aspect]

The observation apparatus in accordance with a seventh aspect of the present invention is arranged such that the control section controls a temperature around the cell or the cell tissue so that the temperature is maintained at 36° C. to 37° C. According to the above configuration, it is possible to suitably observe, over time, even a cell which requires strict control of a culture condition, such as a normal human bronchial epithelial cell, with use of the cell culture vessel.

[Eighth Aspect]

The observation apparatus in accordance with an eighth aspect of the present invention is arranged such that the control section controls a $CO_2$ concentration around the cell or the cell tissue so that the $CO_2$ concentration is maintained at 4.0% to 5.0%. According to the above configuration, it is possible to suitably observe, over time, even a cell which requires strict control of a culture condition, such as a normal human bronchial epithelial cell, with use of the cell culture vessel.

[Ninth Aspect]

The observation apparatus in accordance with a ninth aspect of the present invention may be arranged so as to further include the cell culture vessel in accordance with the fourth aspect. According to the above configuration, it is possible to suitably carry out an observation with use of the cell culture vessel.

[Tenth Aspect]

A fixing tool in accordance with a tenth aspect of the present invention is a fixing tool for fixing a cell culture vessel for accommodating a cell or cell tissue therein, the cell culture vessel including: a frame part which is provided so as to be located at positions that correspond to respective sides of a polyhedral shape; and a window which part is light-transmissive and which is provided so as to be located at positions that correspond to a respective plurality of faces out of faces of the polyhedral shape, the fixing tool including: a holding part which holds the cell culture vessel; and a shaft part which is connected to the holding part and which extends, from any of vertices of the polyhedral shape, outward in a direction that is not parallel to any of lines normal to the faces of the polyhedral shape.

According to the above configuration, even in a case where the cell culture vessel does not have a shaft part, it is possible to rotate the cell culture vessel on the shaft part of the fixing tool while appropriately fixing the cell culture vessel with use of the fixing tool. Thus, it is possible to bring about an effect similar to that brought about by the first aspect. Moreover, the cell culture vessel does not have a shaft part. This is convenient for culture by immersion of the cell culture vessel in a dish or the like.

[Eleventh Aspect]

An observation apparatus in accordance with an eleventh aspect of the present invention is an observation apparatus including: a fixing tool for fixing a cell culture vessel for accommodating a cell or cell tissue therein; and a rotating mechanism which rotates the cell culture vessel, the cell culture vessel including: a frame part which is provided so as to be located at positions that correspond to respective sides of a polyhedral shape; and a window part which is light-transmissive and which is provided so as to be located at positions that correspond to a respective plurality of faces out of faces of the polyhedral shape, the fixing tool including: a holding part which holds the cell culture vessel; and a shaft part which is connected to the holding part and which extends, from any of vertices of the polyhedral shape, outward in a direction that is not parallel to any of lines normal to the faces of the polyhedral shape, the rotating mechanism holding the shaft part and rotating, on the shaft part, the cell culture vessel held by the fixing tool.

According to the above configuration, an effect similar to that brought about by the tenth aspect is brought about.

[Twelfth Aspect]

The observation apparatus in accordance with a twelfth aspect of the present invention may be arranged so as to further include the cell culture vessel in accordance with the eleventh aspect.

According to the above configuration, an effect similar to that brought about by the tenth aspect is brought about.

[Thirteenth Aspect]

The observation apparatus in accordance with thirteenth aspect of the present invention is arranged so as to further include: a chamber in which the cell culture vessel is accommodated; and a control section which controls a culture condition around the cell in the chamber, under which the cell is cultured, or a culture condition around the cell tissue in the chamber, under which the cell tissue is cultured.

According to the above configuration, it is possible to suitably observe, over time, even a cell which requires strict control of a culture condition, such as a normal human bronchial epithelial cell, with use of the cell culture vessel.

[Fourteenth Aspect]

A microscope in accordance with a fourteenth aspect of the present invention may include an observation apparatus in accordance with any one of the fourth to ninth, eleventh, and twelfth aspects. According to the above configuration, it is possible to bring about an effect similar to that brought about by the fourth or seventh aspect.

[Fifteenth Aspect]

An observation method in accordance with a fifteenth aspect of the present invention is a method of observing a cell culture vessel for accommodating a cell or cell tissue, the cell culture vessel including: a frame part which is provided so as to be located at positions that correspond to respective sides of a polyhedral shape; a window part which is light-transmissive and which is provided so as to be located at positions that correspond to a respective plurality of faces out of faces of the polyhedral shape; and a shaft part which extends, from any of vertices of the polyhedral shape, outward in a direction that is not parallel to any of lines normal to the faces of the polyhedral shape, the method including: rotating the cell culture vessel on the shaft part of the cell culture vessel.

According to the above configuration, it is possible to bring about an effect similar to that brought about by the first aspect.

[Sixteenth Aspect]

An observation method in accordance with a sixteenth aspect of the present invention is a method of observing a cell or cell tissue accommodated in a cell culture vessel, the cell culture vessel including: a frame part which is provided so as to be located at positions that correspond to respective sides of a polyhedral shape; and a window part which is light-transmissive and which is provided so as to be located at positions that correspond to a respective plurality of faces out of faces of the polyhedral shape, a fixing tool for fixing the cell culture vessel including: a holding part which holds the cell culture vessel; and a shaft part which is connected to the holding part and which extends, from any of vertices of the polyhedral shape, outward in a direction that is not parallel to any of lines normal to the faces of the polyhedral shape, the method including holding the cell culture vessel with use of the fixing tool and rotating the cell culture vessel on the shaft part.

According to the above configuration, it is possible to bring about an effect similar to that brought about by the first aspect.

[Seventeenth Aspect]

The observation method in accordance with a seventeenth aspect of the present invention is arranged so as to further include controlling a culture condition around the cell in the chamber, under which the cell is cultured, or a culture condition around the cell tissue in the chamber, under which the cell tissue is cultured.

According to the above configuration, it is possible to bring about an effect similar to that brought about by the fifth aspect.

The present invention is not limited to the embodiments, but can be altered by a skilled person in the art within the scope of the claims. The present invention also encompasses, in its technical scope, any embodiment derived by combining technical means disclosed in differing embodiments.

REFERENCE SIGNS LIST

10 Cell culture vessel
11 Frame part
12 Window part
13 Cell or cell tissue
14 Culture gel
15 Protruding part
16 End portion
17 Shaft part (of cell culture vessel)
18 Bearing
20 Fixing tool
22 Holding part
25 Shaft part (of fixing tool)
30, 130 Observation apparatus
31 Z-axis mechanical stage
32 Base
33 Pedestal part
34 Obliquely fixed holder
35 Rotation stage
36 Extending part
37 Collet chuck
38 Stepping motor
39 Controller
41 Lens barrel
42 Microscope stage
51 Dish
60 Light-sheet microscope
61 Mirror
62 Light sheet
63 Laser emitting section
131 Control section
132 Temperature sensor
133 Heater
134 Cooler
135 $CO_2$ concentration sensor
136 $CO_2$ adjuster
137 Chamber
139 Image capturing section
140 Three-axis adjusting mechanism

The invention claimed is:

1. A cell culture vessel for accommodating a cell or cell tissue therein, comprising:
a frame part which is provided so as to be located at positions that correspond to respective edges of a polyhedral shape;
window parts which are light-transmissive and which are provided so as to be located at positions that correspond to a respective plurality of faces out of faces of the polyhedral shape; and
a shaft part which extends, from any of vertices of the polyhedral shape, outward in a direction that is not parallel to any of lines normal to the faces of the polyhedral shape.

2. The cell culture vessel as set forth in claim 1, wherein the shaft part extends along a straight line that passes through the any of the vertices and a center of the cell culture vessel.

3. The cell culture vessel as set forth in claim 1, wherein the polyhedral shape is a hexahedral shape.

4. An observation apparatus comprising
a rotating mechanism which holds a shaft part of a cell culture vessel and which rotates the cell culture vessel on the shaft part, and
the cell culture vessel,
the cell culture vessel being for accommodating a cell or cell tissue therein,
the cell culture vessel comprising:
a frame part which is provided so as to be located at positions that correspond to respective edges of a polyhedral shape;
window parts which are light-transmissive and which are provided so as to be located at positions that correspond to a respective plurality of faces out of faces of the polyhedral shape; and
the shaft part which extends, from any of vertices of the polyhedral shape, outward in a direction that is not parallel to any of lines normal to the faces of the polyhedral shape.

5. The observation apparatus as set forth in claim 4, further comprising:
a chamber in which the cell culture vessel is accommodated; and
a control section which controls a culture condition around the cell in the chamber, under which the cell is cultured, or a culture condition around the cell tissue in the chamber, under which the cell tissue is cultured.

6. The observation apparatus as set forth in claim 5, wherein the control section controls at least one of a temperature and $CO_2$ (carbon dioxide concentration) around the cell or at least one of a temperature and a $CO_2$ concentration around the cell tissue.

7. The observation apparatus as set forth in claim 5, wherein the control section controls a temperature around the cell or the cell tissue so that the temperature is maintained at 36° C. to 37° C.

8. The observation apparatus as set forth in claim 5, wherein the control section controls a $CO_2$ concentration around the cell or the cell tissue so that the $CO_2$ concentration is maintained at 4.0% to 5.0%.

9. A fixing tool for fixing a cell culture vessel for accommodating a cell or cell tissue therein,
the cell culture vessel comprising:
a frame part which is provided so as to be located at positions that correspond to respective edges of a polyhedral shape; and
window parts which are light-transmissive and which are provided so as to be located at positions that correspond to a respective plurality of faces out of faces of the polyhedral shape,
the fixing tool comprising:
a holding part which holds the cell culture vessel; and
a shaft part which is connected to the holding part and which extends, from any of vertices of the polyhedral shape, outward in a direction that is not parallel to any of lines normal to the faces of the polyhedral shape.

10. An observation apparatus comprising:
a fixing tool for fixing a cell culture vessel for accommodating a cell or cell tissue therein;
a rotating mechanism which rotates the cell culture vessel, and
the cell culture vessel,
the cell culture vessel comprising:
a frame part which is provided so as to be located at positions that correspond to respective edges of a polyhedral shape; and window parts which are light-transmissive and which are provided so as to be located at positions that correspond to a respective plurality of faces out of faces of the polyhedral shape, the fixing tool comprising:

a holding part which holds the cell culture vessel; and a shaft part which is connected to the holding part and which extends, from any of vertices of the polyhedral shape, outward in a direction that is not parallel to any of lines normal to the faces of the polyhedral shape, the rotating mechanism holding the shaft part and rotating, on the shaft part, the cell culture vessel held by the fixing tool.

11. The observation apparatus as set forth in claim 10, further comprising:

a control section which controls a culture condition around the cell in the chamber, under which the cell is cultured, or a culture condition around the cell tissue in the chamber, under which the cell tissue is cultured.

12. A method of observing a cell or cell tissue accommodated in a cell culture vessel, the cell culture vessel comprising:

a frame part which is provided so as to be located at positions that correspond to respective edges of a polyhedral shape;

window parts which are light-transmissive and which are provided so as to be located at positions that correspond to a respective plurality of faces out of faces of the polyhedral shape; and a shaft part which extends, from any of vertices of the polyhedral shape, outward in a direction that is not parallel to any of lines normal to the faces of the polyhedral shape, the method comprising rotating the cell culture vessel on the shaft part of the cell culture vessel.

13. A method of observing a cell or cell tissue accommodated in a cell culture vessel, the cell culture vessel comprising:

a frame part which is provided so as to be located at positions that correspond to respective edges of a polyhedral shape; and window parts which are light-transmissive and which are provided so as to be located at positions that correspond to a respective plurality of faces out of faces of the polyhedral shape, a fixing tool for fixing the cell culture vessel comprising:

a holding part which holds the cell culture vessel; and a shaft part which is connected to the holding part and which extends, from any of vertices of the polyhedral shape, outward in a direction that is not parallel to any of lines normal to the faces of the polyhedral shape, the method comprising holding the cell culture vessel with use of the fixing tool and rotating the cell culture vessel on the shaft part.

14. The method as set forth in claim 12, wherein:

the cell culture vessel is accommodated in a chamber; and the method further comprises controlling a culture condition around the cell in the chamber, under which the cell is cultured, or a culture condition around the cell tissue in the chamber, under which the cell tissue is cultured.

15. A microscope comprising an observation apparatus comprising a rotating mechanism which holds a shaft part of a cell culture vessel and which rotates the cell culture vessel on the shaft part, the cell culture vessel being for accommodating a cell or cell tissue therein, the cell culture vessel comprising:

a frame part which is provided so as to be located at positions that correspond to respective edges of a polyhedral shape;

window parts which are light-transmissive and which are provided so as to be located at positions that correspond to a respective plurality of faces out of faces of the polyhedral shape; and the shaft part which extends, from any of vertices of the polyhedral shape, outward in a direction that is not parallel to any of lines normal to the faces of the polyhedral shape.

16. A microscope comprising an observation apparatus comprising:

a fixing tool for fixing a cell culture vessel for accommodating a cell or cell tissue therein;

a rotating mechanism which rotates the cell culture vessel, the cell culture vessel comprising:

a frame part which is provided so as to be located at positions that correspond to respective edges of a polyhedral shape; and window parts which are light-transmissive and which are provided so as to be located at positions that correspond to a respective plurality of faces out of faces of the polyhedral shape, the fixing tool comprising:

a holding part which holds the cell culture vessel; and a shaft part which is connected to the holding part and which extends, from any of vertices of the polyhedral shape, outward in a direction that is not parallel to any of lines normal to the faces of the polyhedral shape, the rotating mechanism holding the shaft part and rotating, on the shaft part, the cell culture vessel held by the fixing tool.

* * * * *